United States Patent [19]

Raterman

[11] Patent Number: 5,458,721
[45] Date of Patent: Oct. 17, 1995

[54] DUAL FORMAT ADHESIVE PROCESS FOR INTERMITTENTLY DISRUPTING PARALLEL LINES OF ADHESIVE TO FORM ADHESIVE BANDS

[75] Inventor: John Raterman, Lawrenceville, Ga.

[73] Assignee: Nordson Corporation, Westlake, Ohio

[21] Appl. No.: 310,680

[22] Filed: Sep. 22, 1994

Related U.S. Application Data

[62] Division of Ser. No. 865,094, Apr. 8, 1992, Pat. No. 5,382,312.

[51] Int. Cl.[6] ......................................................... B32B 7/14
[52] U.S. Cl. .................... 156/291; 156/244.11; 156/290; 156/164; 427/208.2; 427/208.6; 427/422; 427/424
[58] Field of Search ......................................... 156/500, 291, 156/290, 578, 244.11, 164, 356, 244.12, 163; 239/296–300, 412, 416, 399, 426; 118/300, 313, 315; 427/208.6, 207.1, 208.2, 422, 424

[56] References Cited

U.S. PATENT DOCUMENTS

| | | |
|---|---|---|
| 3,341,124 | 9/1967 | Barnes . |
| 3,825,379 | 7/1974 | Lohkamp et al. . |
| 4,687,137 | 8/1987 | Boger et al. . |
| 4,711,683 | 12/1987 | Merkatoris . |
| 4,714,647 | 12/1987 | Shipp, Jr. et al. . |
| 4,720,252 | 1/1988 | Appel et al. . |
| 4,815,660 | 3/1989 | Boger . |
| 4,849,049 | 7/1989 | Colton . |
| 4,874,451 | 10/1989 | Boger et al. . |
| 4,891,249 | 1/1990 | McIntyre . |
| 4,891,249 | 1/1990 | McIntyre . |
| 4,957,783 | 9/1990 | Gabryszewski . |
| 4,983,109 | 1/1991 | Miller et al. . |
| 4,995,333 | 2/1991 | Keller et al. . |
| 5,030,303 | 7/1991 | Cucuzza . |
| 5,064,492 | 11/1991 | Friesch ............................. 427/208.2 X |

OTHER PUBLICATIONS

"The Waistband Phenomenon" by Frederic S. McIntyre, Acumeter Laboratories, Marlborough, Mass.

Primary Examiner—Jeff H. Aftergut
Attorney, Agent, or Firm—Wood, Herron & Evans

[57] ABSTRACT

A laminate is made by applying a plurality of parallel fine lines of adhesive to a first web, intermittently agitating the adhesive prior to deposition to intermingle the adhesive to form spaced apart bands extending across the fine lines, and then applying a second web over the adhesive to join the webs together. The intermittent cross bands prevent migration of particles and leakage along said fine lines. When diapers are made from the laminate, waistbands are formed in the areas of the cross bands. Apparatus is disclosed.

6 Claims, 3 Drawing Sheets

DUAL FORMAT ADHESIVE PROCESS FOR INTERMITTENTLY DISRUPTING PARALLEL LINES OF ADHESIVE TO FORM ADHESIVE BANDS

This application is a divisional of application Ser. No. 07/865,094, filed Apr. 8, 1992, now U.S. Pat. No. 5,382,312.

This invention relates to adhesive application for lamination and more particularly to adhesive applicators and methods for improved adhesive application and products.

It is well known to adhere two webs or sheets together by applying parallel beads or fine lines of adhesives to one web or sheet and then combining the two webs or sheets so the adhesive can bind them together. One use of this technique is found in the manufacture of disposable diapers. These usually include a moisture impervious polyethylene backing, and a non-woven, absorbent pad sometimes referred to as "fluff".

In making such diapers, parallel beads or fine lines of adhesive are deposited in a machine direction onto a moving web of polyethylene backing material. The non-woven web or fluff is laid on the plastic web so the elongated adhesive beads secure it to the backing. Leg holes are then cut in the laminate and the diaper is otherwise finished. Such a technique is described in U.S. Pat. No. 4,874,451, which is incorporated herein by reference.

One of the difficulties in using such a technique in manufacturing diapers is that the adhesive beads tend to define channels on the polyethylene backing. Particles of super absorbent non-woven material can migrate through these channels to the diaper's leg holes or waist areas where they escape. The channels may lead to other problems such as leaking. Additional manufacturing treatment or components are required to seal off these channels.

It is also known in the diaper manufacturing industry to apply the adhesive to the plastic backing web in a "swirl" pattern, or in random "fibrous" depositions. Overlapping swirls could be applied, for example, by apparatus such as that disclosed in U.S. Pat. No. 4,983,109, which is incorporated herein by reference. Such swirl or fibrous adhesive applications provide a more "homogeneous" or continuous adhesive blanket and do not create the channels noted above. They thus provide continuous adhesion, both in the machine direction and in the cross-machine direction across the backing. This inhibits moisture leaking or particle migration. Also, these processes permit cooler deposition of hot melt adhesives on the plastic backing, thus avoiding burn through. Accordingly, the gage of the backing can be reduced, with attendant cost savings.

Nevertheless, the parallel bead process does provide certain beneficial adherance and process characteristics not obtained by the "swirling" process. For example, the beads remain at a somewhat higher temperature when applied and in certain applications generate greater adhesion or bonding strength. These characteristics will continue to be desirable in certain diaper applications, disposable pads, and in other products. There is a continuing need, however, to prevent migration of moisture and particles along the beads, i.e. along the length or in the machine direction of the product.

Accordingly, it is one objective of this invention to provide an improved fine line adhesive application which prevents moisture or particle migration to undesirable outlets at the line ends.

A further objective of the invention has been to provide apparatus for applying an improved adhesive application to a substrate.

A further objective of the invention has been to provide an improved article comprising a flexible backing sheet and an absorbent pad adhered thereto with fine lines of adhesive.

A further objective has been to provide an improved method for securing fluff to a flexible backing.

A further objective of the invention has been to provide an improved method for adhering one substrate to another.

A further objective of the invention has been to provide an improved method for applying adhesive to a substrate.

To these ends, a preferred embodiment of the invention includes an adhesive application comprising a plurality of parallel beads or fine line deposition of adhesive along a substrate in a machine direction, and a swirl pattern or random fibrous adhesive deposition in a cross-machine direction on the substrate at intermittent, selected distances along the fine line deposition. The swirl or fibrous deposition joins the fine lines and provides a migration barrier across the fine lines.

A fine line applicator, having a plurality of fine line or elongated bead producing nozzles, is provided with air jet means associated with each nozzle. These are intermittently activated to selectively swirl or disrupt the emanating bead into a swirl pattern or into a random fibrous orientation, thus producing a homogeneous or continuous adhesive band across the fine lines. This band serves as a barrier to migration along the lines.

An air source is selectively controlled so as to discontinue air flow to the air jet means when fine parallel lines are to be deposited, and to supply air flow at selected times when desired to produce a transverse band of swirl pattern or random fibrous adhesive to seal off the fine lines.

These sealing bands are produced, for example, in the areas which will respectively form the leg holes or waist of a diaper to prevent migration of moisture or particles from between the backing and the fluff. At the same time, the enhanced bonding characteristics of the fine line adhesive are attained, yet without the need to otherwise treat or apply additional components to stop deleterious migration.

Accordingly, a fine line applicator for depositing fine lines of adhesives is provided with cyclic air jet means to produce swirls or fibrous depositions cross-joining the fine lines at selected intermittent locations.

The invention provides advantages of both prior and previously exclusive techniques, i.e. the adhesion benefits of fine line deposition with the migration preventing continuous adhesive blanket deposition.

These and other advantages will become readily apparent from the following description of a preferred embodiment of the invention and from the drawings in which:

FIG. 1A is a diagrammatic end view of the adhesive applicator of FIG. 1 illustrating fine line adhesive deposition;

FIG. 1B is a diagrammatic end view of the adhesive applicator of FIG. 1 illustrating adhesive swirl or random fibrous deposition;

SPECIFICATION

Figure 1:
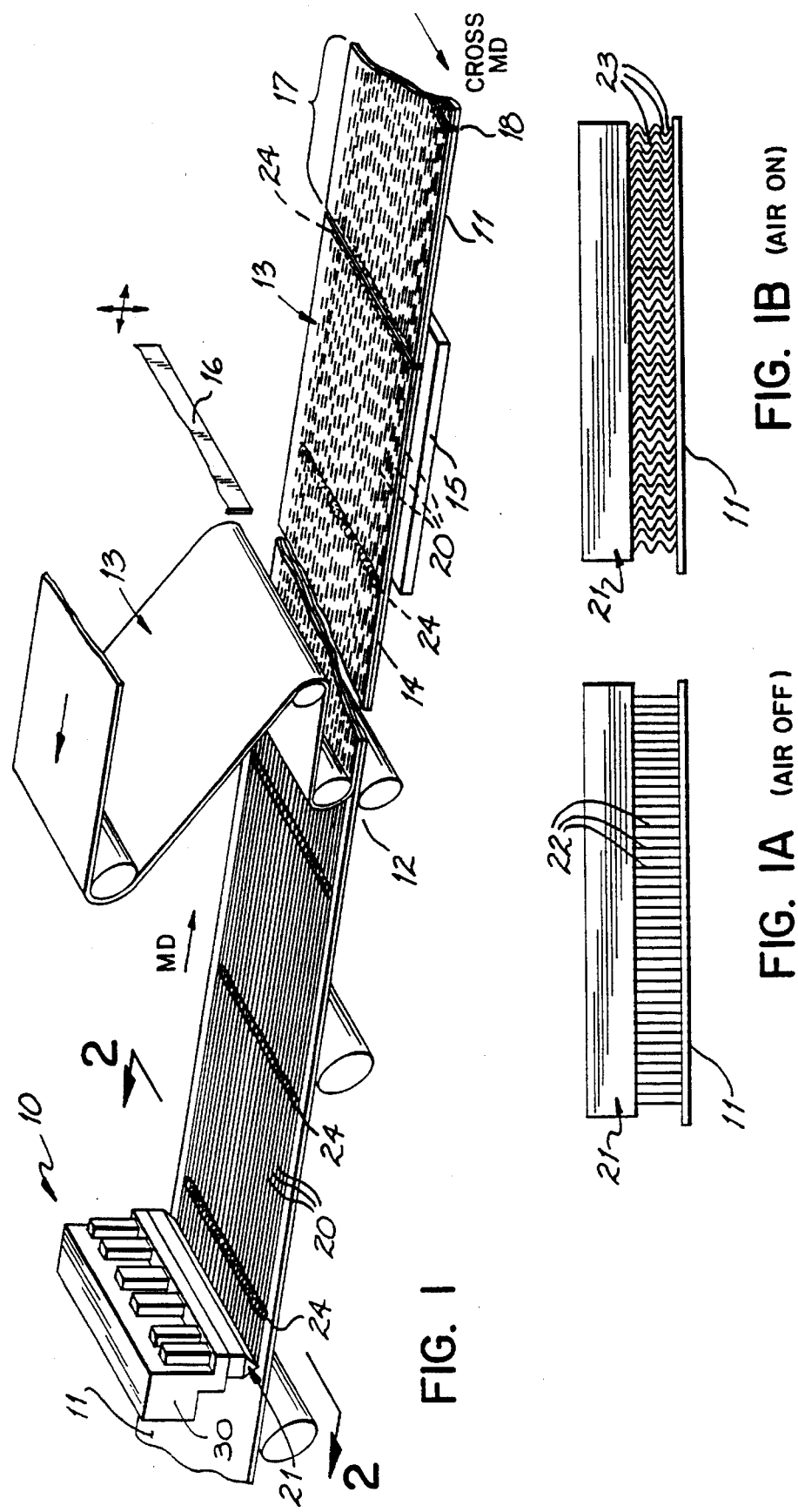
FIG. 1 is a perspective view of an adhesive application process, application apparatus and article according the invention.

Turning now to the drawings, it will be appreciated that the invention contemplates improved methods and apparatus for producing an improved laminate structure, particularly useful in the manufacture of disposable products, such as absorbent diapers, pads and other similar products. The manufacturing process for the laminate is diagrammatically illustrated in FIG. 1.

An applicator head 10 is operable to supply adhesive to one side of an elongated web comprising a flexible backing 11, such as a thin, moisture impervious, polyethyene film. The moving web is then rolled through a nip at 12, where a web 13 of absorbent fluff material is combined with the backing web, such that the adhesive holds the two webs together. Thereafter, the combined moving laminate 14 is conveyed in a machine direction to a cutting platen 15. A knife 16 severs the laminate within the area defined by crossbands of adhesive as will be described. While the laminate 14 and the cut-off articles 17 are shown in FIG. 1 as being rectangular, it will be appreciated they could be of other longitudinal shapes, such as diapers with cut out leg holes or other pad configurations or the like.

It will also be appreciated that the fluff 13 is preferably a non-woven, absorbent material, such as that utilized in disposable diapers, for example, but could be other forms of material, depending on the desired application.

The invention contemplates the application of adhesive by the applicator head 10 onto the first web or substrate 11, primarily in a plurality of fine lines of adhesive 20, as shown in FIG. 1. These are deposited onto the substrate 11 from a slot die nozzle 21. Adhesive emanates from the slot die 21 in the form of a plurality of adhesive beads, such as at 22 (see FIG. 1a). When the beads contact the moving substrate 11 thereunder, they are deposited on that substrate in the form of a plurality of parallel, fine lines of adhesive 20.

It will be appreciated, as used above, the term "beads" is used for descriptive purposes in this application to refer to the adhesive emanating from the slot die nozzle 21 in the area between the slot die nozzle and the substrate 11. On the other hand, the term "fine line" is used generally in this application to describe the adhesive as it is deposited on the underlying substrate 11. This distinction is made in this application for the purpose of description only. It will be appreciated that the elongated parallel strips of adhesive on the substrate 11 could also be referred to as beads of adhesive on the substrate.

The slot die nozzle 21 is provided with means for intermittently agitating the beads 22 (FIG. 1A) into a swirl or a random fibrous pattern, as illustrated diagrammatically in FIG. 1B. Such agitated beads are diagrammatically indicated at 23 in FIG. 1B. When the beads are agitated, they still descend to, and are deposited on the substrate 11, but not in the form of parallel fine lines of adhesives. Instead, the agitated beads commingle in a swirl pattern or in a random fibrous orientation. Such swirl or random fibrous lines constitute a continuation of the fine parallel lines, but are intermingled with each other so as to join the adjacent parallel fine lines in a band of adhesive 24. Such bands are selectively and intermittently spaced in the cross machine direction, i.e. across the web 11, transversely to the machine direction.

When the beads 22 are deposited in parallel, fine lines on the substrate 11, the parallel fine lines 20 are spaced apart and define channels therebetween. Nevertheless, the intermingling of agitated beads 23 in the swirl or fibrous pattern of the band 24 seals off the spaces or channels between the fine lines 20 so that no particles of fluff material or other particles can migrate along those fine lines past the band 24. Accordingly, the bands of adhesive 24 serve to interrupt any migration of particles along the substrate 11 in the areas between the fine lines 20 of adhesive.

It will be appreciated that when the laminate 14 is cut by knife 16, that cut is disposed within the band 24, so that each end of the separated laminates 17 have an edge band of intermingled swirled or fibrous adhesive extending in a cross machine direction across the ends of the fine lines 20. This interrupts any migration of particles between the fine lines 20 outwardly at the edge 18 of the cut-off laminates 17.

It will also be appreciated that when the adhesive beads emanating from the nozzle 21 are swirled or otherwise agitated to form a random fibrous pattern, they still constitute a continuation of the lines of adhesive which are already laid down on the substrate 11, so that a migration barrier is formed by that band across the adhesive lines.

Figure 2:
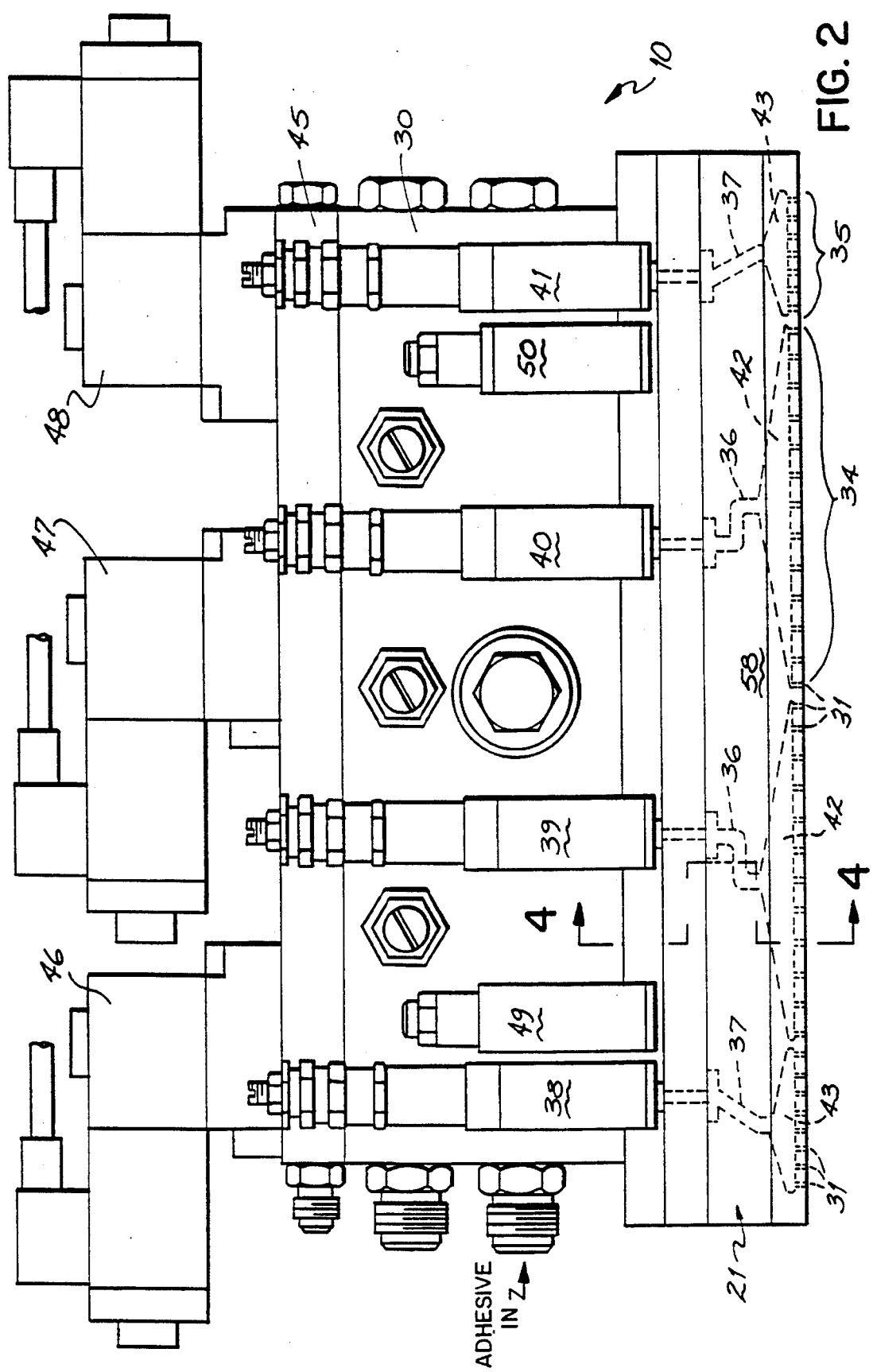
FIG. 2 is a schematic elevational end view of the adhesive applicator taken along lines 2—2 of FIG. 1.

Turning now to a further description of the apparatus for producing the parallel fine lines of adhesives with the intermittent cross bands, reference is made to FIG. 2, which constitutes a diagrammatic elevational end view of the adhesive applicator 10. The applicator 10 includes a head 30 and a slot die 21. With the exception of the details of FIG. 4, the applicator 10 is essentially like that described in detail in U.S. Pat. No. 4,874,451. Reference is also made to U.S. Pat. No. 3,825,379, and the melt blowing die disclosed therein.

The slot die 21 includes a plurality of adhesive grooves or nozzles 31, defined by complimentary relieved areas in die halves 32 and 33. The adhesive outlet grooves 31 may be ganged in sections, such as sections 34, 35 (FIGS. 2 and 3) for the generation of a plurality of adhesive beads. These sections can be controlled independently, as described in U.S. Pat. No. 4,874,451 for particular applications.

Figure 3:
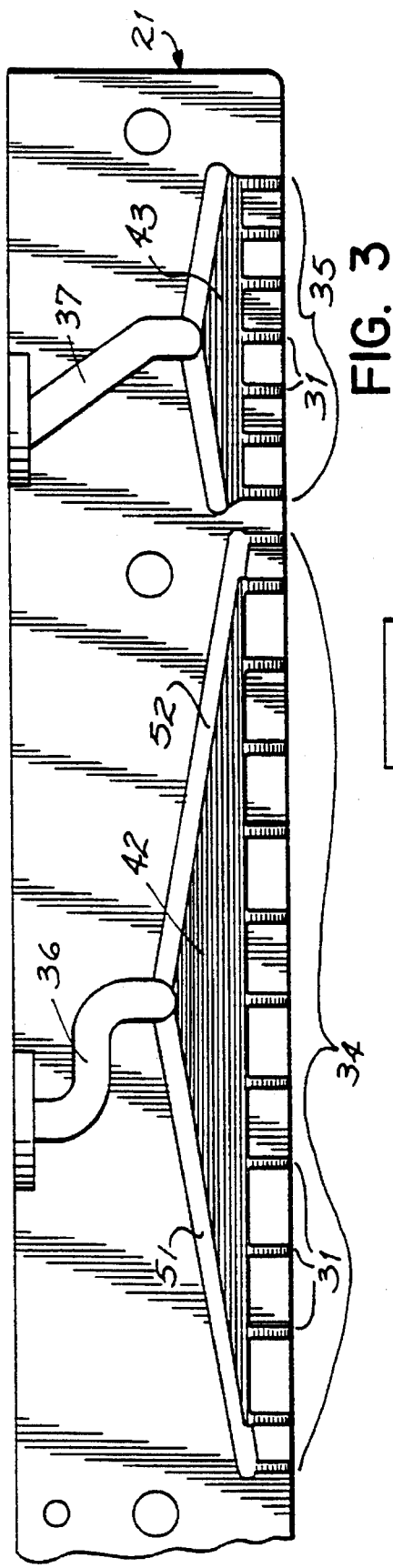
FIG. 3 is a view similar to FIG. 2 but showing the fine line producing grooves in the adhesive applicator.
Figure 4:
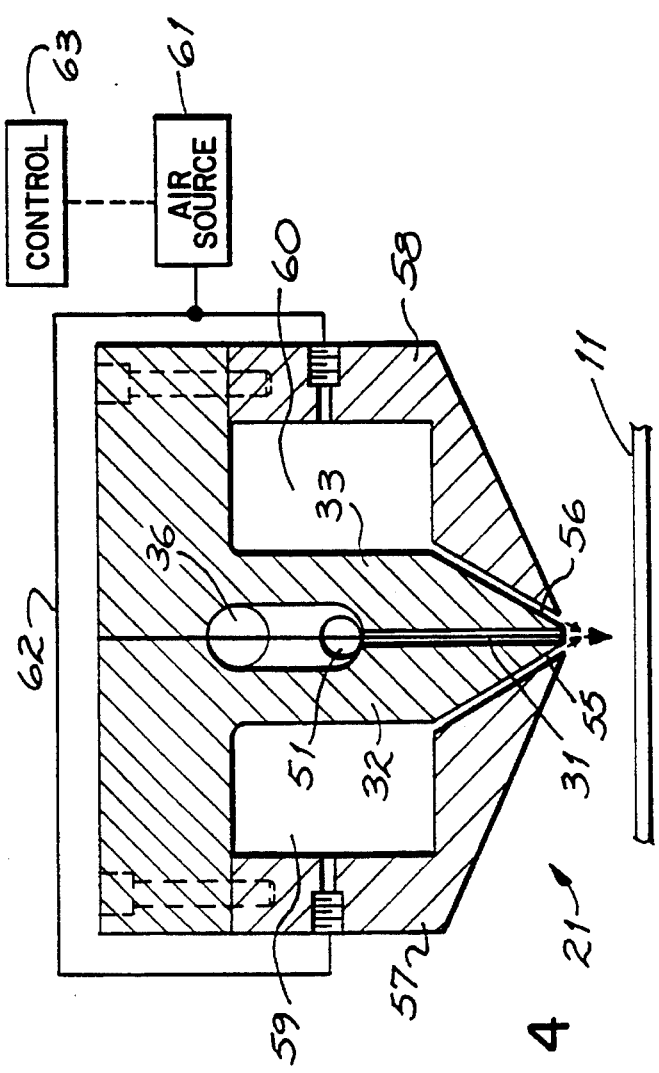
FIG. 4 is an enlarged cross-sectional view taken along lines 4—4 of FIG. 2 and illustrating also an adhesive receiving substrate.

Each section 34, 35 is fed by a respective inlet passage such as at 36 or 37. Adhesive is conveyed from an adhesive control valve, such as 38, 39, 40 or 41, to respective sections also as described in U.S. Pat. No. 4,874,451. Valves 40, 41 feed respective sections 34, 35 shown herein. The inlets 36, 37 feed respective triangular portions 42 or 43 for distribution of adhesive to the adhesive outlets 31. Referring to FIGS. 3 and 4 then, each of the sections of adhesive emanating grooves 31 are fed by a respective triangular section 42, 43. Inlets 36 and 37 feed the triangular relieved areas 42 and 43. The inlets are also connected to the runners or passages 51, 52.

The valves 38–41 are operated through a valve air manifold 45 by one or more air solenoids 46–48, as described in the preceding U.S. Pat. No. 4,874,451. Recirculation valves 49 and 50 are used as described in said patent for adhesive control when the outside sections or banks of orifices are to be shut off, such as when the underlying substrate moving under the slot die is in an area corresponding to the position where leg holes will be cut out from the resulting diapers.

It will be appreciated that the valves 38–41 are appropriately connected via manifolds and passages to control circuits for operating the valves, such as air passages, and to adhesive manifolds for selective control of adhesive flow to the sections of adhesive emanating grooves or nozzles.

The slot die 21, according to the invention, is provided with air jet means 55, 56, defined as elongated passageways in manifold covers 57 and 58. Air chambers 59 and 60 are interconnected to a source of pressurized air 61 through a pneumatic line 62. Pressurized air source 61 is controlled by an electric or pneumatic solenoid controller means 63 of any suitable type for operating the air source to selectively pressurize line 62 and chambers 59 and 60 with pressurized air. When pressurized, this causes a flow of air through the air jet means or passages 55, 56, to impinge on a bead of adhesive 23 emanating from the outlet 31 (FIG. 1B) to agitate that adhesive bead and cause it to form a swirl or spiral, or to be deposited in a random fibrous orientation across the substrate 11 in a band of adhesive 24, such as shown in FIG. 1. It should be appreciated that the air jet means 55, 56 impinge tangentially on the bead in one form, and may themselves be angularly oriented, such that their axes do not intersect, but are directed to cause the bead to form a spiral such as, for example, the air jets in U.S. Pat. No. 4,983,109.

Of course, the air jet means 55, 56 can be provided in any suitable orientation to cause the desired swirl or agitation to produce a random fibrous pattern in a cross band, as illustrated in FIG. 1. For example, air jet means such as that described in U.S. Pat. No. 4,815,660, U.S. Pat. No. Re. 33,481, or in applicant's co-pending application Ser. No. 07/783,989, filed Oct. 29, 1991, could be used. Also, any other form of means to selectively intermittently agitate the adhesive emanating from the outlet 31 to cause it to deposit to seal off the gaps between the lines on the underlying substrate could be used. For example, a cone-shaped air passage with vanes for swirling the air and surrounding the adhesive orifice could be used, as well as elongated air slots or other means.

It will be appreciated that the band of adhesive, which is deposited on the substrate 11 when the air jets are operated, is in the cross machine or transverse direction across the substrate. The agitated beads themselves are simply a continuation of the adhesive lines which are already deposited on the substrate. The swirls or fibrous pattern in the band 24 intermingle with adjacent adhesive beads and/or lines of adhesive on the substrate, so as to bridge the spaces or distances between the parallel fine lines of adhesive, which were being deposited before the flow of air was initiated, in order to close off any spaces between those fine lines. In the deposited pattern, this interrupts any migration of particles along those fine lines between the adhered laminate substrates 11 and 13.

Of course, it will also be appreciated that the control means 63 is operated to intermittently pressurize the chambers 59, 60, to intermittently cause air flow through the air jet means 55, 56. The timing of these intermittent applications of air to the bead from the jets 55, 56, is predetermined so that the generation of the bands 24 in the cross machine direction on the substate 11 are deposited in those areas of the substrate which will be cut by the knife 16 (FIG. 1).

Also it will be appreciated that such transverse or cross machine direction bands can be generated at other predetermined positions. When diapers are made, for example, these bands can be oriented in the areas surrounding the web material where the leg holes are to be cut. This interrupts migration of particles outside the edge of the laminate at those particular areas.

Accordingly, it will be appreciated that the invention provides apparatus and methods for depositing a predetermined adhesive on a substrate and for producing a laminate of two substrates with an improved adhesive disposition therebetween.

Accordingly, one substrate is adhered to the flexible backing substrate 11 by means of elongated, parallel fine lines of adhesive, which produce excellent bonding characteristics of the one substrate to the other, while at the same time the intermittently spaced bands 24 serve to join the elongated adhesive lines and to interrupt any migration or particles therealong. Manufacturing, cutting or other processes can be carried out in the area in which the bands 24 are deposited, to prevent the migration of particles of non-woven material of the substrate 13, for example, outside the edge of the finished laminate article at the edge. Accordingly, the article exhibits good bonding characteristics provided by a parallel fine line adhesive process, without the disadvantage of particle migration or the necessity to conduct other further manufacturing techniques or add additional elements to the laminate.

It will be appreciated that the structure of the slot die can be like that as shown in U.S. Pat. No. 3,825,379, with the appropriate slot widths to produce the desired fine lines of adhesive on an underlying substrate when the air is turned off, according to the invention herein.

It will also be appreciated that the invention is useful in a system, such as that disclosed in U.S. Pat. No. 4,874,451, where it is desired to provide a band of adhesive in the cross machine direction to join or seal off the ends of the fine line adhesive applied to the substrate. This occurs in one application such as diapers, in the areas to comprise the waistband and the leg holes of the diapers.

Accordingly, the invention provides for the realization of the greater adhesive and bonding characteristics of the fine line adhesive deposition process, but also provides the benefits of the swirl or random fibrous pattern process all in the same laminate by selectively controlling the application of air to the slot dies which are operable to emanate a bead for fine line deposition. The swirl or random fibrous bands can be created at any predetermined areas on the substrate. Moreover, instead of being continuous across the substrate, such bands could be formed in any pre-selected length by separating the air chambers 59 and 60, and dedicating them respectively to air jets serving each groove 31. With appropriate valving, this can be used to cause the bead emanating from that groove to swirl or move randomly, or to deposit in a straight line. Finally, it will be appreciated that while the swirl pattern or a random fibrous orientation may be preferred, either is possible, depending upon the orientation of the air jets 55, 56 and the nature of the air jet flow. Other forms of intermittent agitation, such as mechanical or other expedients, could be utilized as well to cause the emanating beads to intermingle, at least as deposited on the substrate, to produce the band 24, as described herein.

Accordingly, these and other modifications and advantages will be readily apparent to one of ordinary skill without departing from the scope of the invention, and the applicant intends to be bound only by the claims appended hereto:

I claim:

1. A method of applying adhesive to a substrate for use in laminating the substrate to another component and comprising the steps of:

depositing a plurality of substantially parallel lines of adhesive onto a substrate; and intermittently agitating said adhesive lines prior to deposition on said substrate to cross-join parallel lines of adhesive deposited on the substrate to form bands of adhesive at spaced locations across said parallel lines.

2. A method of adhering two substrates to form a laminate article including the steps of:

depositing a plurality of substantially parallel lines of adhesive on a first substrate;

intermittently disturbing the depositing of parallel lines of adhesive to cause the adhesive to form an adhesive band across said lines in predetermined locations on said first substrate; and combining a second substrate to said first substrate with said adhesive lines and bands therebetween, bonding said substrates together with said bands preventing migration of particles intermittently along said lines.

3. A method for manufacturing a laminate for use in making disposable diapers comprising a flexible backing and fluff, the method comprising the steps of:

depositing a plurality of parallel lines of adhesive on a web comprising said backing;

intermittently interrupting said depositing step and causing said adhesive to intermingle between said lines to produce an adhesive band across said lines in predetermined locations on said backing; and combining said fluff with said backing with said adhesive therebetween bonding said fluff to said backing, said adhesive bands interrupting migration of particles along said lines.

4. A method of adhesively combining two substrates including the steps of:

operating a plurality of nozzles to produce a plurality of beads of adhesive;

depositing said plurality of adhesive beads on a first substrate in a plurality of parallel lines of adhesive thereon;

intermittently agitating said beads as they emanate from said nozzles to intermingle said beads and to deposit on said first substrate a band of adhesive across said lines; and combining a second substrate onto said first substrate with said adhesive bonding said substrates together.

5. A method as in claim 4 wherein said agitating step includes intermittently impinging on said beads at least one air stream to swirl said beads into a spiral to deposit an adhesive pattern of overlapping swirls across said first substrate.

6. A method as in claim 4 wherein said agitating step includes intermittently impinging a flow of air on said beads to produce a band of random fibrous adhesive lines across said substrate.

* * * * *